United States Patent
Kannan et al.

(10) Patent No.: US 9,688,599 B2
(45) Date of Patent: Jun. 27, 2017

(54) PRODUCTION OF MIXED ALDOL PRODUCTS FROM THE PRODUCTS OF HYDROFORMYLATION REACTIONS

(71) Applicant: Texmark Chemicals, Inc., Galena Park, TX (US)

(72) Inventors: Rajeshwari Kannan, Galena Park, TX (US); Rebecca L. Rosas, Galena Park, TX (US)

(73) Assignee: Texmark Chemicals, Inc., Galena Park, TX (US)

(*) Notice: Subject to any disclaimer, the term of this patent is extended or adjusted under 35 U.S.C. 154(b) by 0 days.

(21) Appl. No.: 14/689,711

(22) Filed: Apr. 17, 2015

(65) Prior Publication Data

US 2015/0299081 A1    Oct. 22, 2015

Related U.S. Application Data

(60) Provisional application No. 61/981,558, filed on Apr. 18, 2014.

(51) Int. Cl.
*C07C 45/74* (2006.01)
*C07C 45/72* (2006.01)

(52) U.S. Cl.
CPC .............. *C07C 45/74* (2013.01); *C07C 45/72* (2013.01)

(58) Field of Classification Search
CPC .................................................... C07C 45/72

USPC ........................................ 568/463, 461, 462
See application file for complete search history.

(56) References Cited

U.S. PATENT DOCUMENTS

| 6,090,986 A | 7/2000 | Godwin et al. |
| 6,340,778 B1 | 1/2002 | Bueschken et al. |
| 2002/0161264 A1 | 10/2002 | Wiese et al. |
| 2011/0046420 A1 | 2/2011 | Kramarz et al. |
| 2012/0172624 A1 | 7/2012 | Grass et al. |

OTHER PUBLICATIONS

International Search Report and Written Opinion for International Application No. PCT/US15/26728.
International Preliminary Report on Patentability for International Application No. PCT/US2015/026728 dated Oct. 27, 2016.

*Primary Examiner* — Elvis O Price
(74) *Attorney, Agent, or Firm* — Tumey L.L.P.

(57) ABSTRACT

A method for producing mixed aldol products from the products of hydroformylation reactions. In one embodiment, the method comprises mixing hydroformylation reaction products comprising aldehydes with a catalyst inside a reactor to create a mixture. The method also includes agitating the mixture at a temperature in a range of between about 200° F. to about 275° F. to create a reacted mixture. The reacted mixture is then cooled in the reactor to create an organic phase and an aqueous phase. The organic phase is pumped out of the reactor and may then be transferred to a distillation tower. The organic phase may be distilled until any mixed aldol products are isolated, wherein the mixed aldol products may be subsequently removed.

20 Claims, 3 Drawing Sheets

PRODUCTION OF MIXED ALDOL PRODUCTS FROM THE PRODUCTS OF HYDROFORMYLATION REACTIONS

CROSS-REFERENCE TO RELATED APPLICATIONS

This application claims priority to U.S. Provisional Patent Application Ser. No. 61/981,558, filed on Apr. 18, 2014, titled "Production of Mixed Aldol Products from the Products of Hydroformylation Reactions," the entire disclosure of which is incorporated herein by reference.

STATEMENT REGARDING FEDERALLY SPONSORED RESEARCH OR DEVELOPMENT

Not applicable.

BACKGROUND OF THE INVENTION

Field of the Invention

The present embodiments relate to the production of mixed aldol products, and more particularly, to methods and systems for producing mixed aldol products from the products of hydroformylation reactions.

Background of the Invention

Aldol condensation comprises the reaction of aldehydes and the elimination of water. Two molecules of aldehyde react producing one molecule of a dimer unsaturated aldehyde, the aldol product, with a concurrent elimination of a molecule of water. The reactants of the aldol condensation reaction may be two of the same species of aldehyde, or may be two different aldehyde species. The products of aldol condensation may comprise cross-aldol products when two different aldehyde species react or self-aldol products when two of the same aldehyde species react; these aldol condensation reactions produce the various type of aldol products, which are referred to herein as "mixed aldol products" (i.e. $C_6$-$C_{20}$ α,β-unsaturated aldehydes). The mixed aldol products may comprise unsaturated aldehydes with flashpoints greater than 110° F. Hydroformylation reactions may produce side streams containing mixtures of $C_2$-$C_6$ aldehydes. These mixtures of $C_2$-$C_6$ aldehydes may also be products of the downstream reactions of hydroformylation products. These hydroformylation reaction products (e.g., $C_2$-$C_6$ aldehyde mixtures) may be used as reactants in the aldol condensation reactions to produce the mixed aldol products.

Generally, hydroformylation reactions may be used to produce aldehydes, which may subsequently be hydrogenated to alcohols for industrial applications. Some of the products of these reactions (including any by-products, co-products, etc.) may have limited industrial use, for example, as boiler fuel or as incineration agents to burn industrial waste. These hydroformylation reaction products may generally be considered to be undesirable products. As undesirable products, the low-value uses for these hydroformylation reaction products may not be the most economical or efficient use of their potential.

Attempts to produce desirable, high-value reagents and/or uses from the hydroformylation reaction products have been attempted previously. However, these methods may have increased costs associated with their conversion to desirable products, thus limiting their use (e.g., reduction of aldehydes to their corresponding alcohols followed by purification by distillation). Further, some of these methods may produce large amounts of products requiring tedious distillations to produce a marketable product. The economics of which are generally not feasible.

Consequently, there is a need for an efficient and economical method for producing desirable products and fuel sources from the low value product mixtures of hydroformylation reactions.

BRIEF SUMMARY OF SOME OF THE PREFERRED EMBODIMENTS

These and other needs in the art are addressed in one embodiment by a method for producing mixed aldol products from products of hydroformylation reactions, the method comprises mixing hydroformylation products comprising aldehydes with a catalyst inside a reactor to create a mixture and agitating the mixture at a temperature in a range of between about 200° F. to about 275° F. to create a reacted mixture. The method further comprises cooling the reaction mixture in the reactor to phase separate the reacted mixture into an organic phase and an aqueous phase, then removing the organic phase out of the reactor, transferring the organic phase to a distillation tower, distilling the organic phase until mixed aldol products are isolated, and then removing the mixed aldol products.

These and other needs in the art are addressed in another embodiment that comprises a method for producing mixed aldol products from products of hydroformylation reactions. The method comprises mixing hydroformylation products comprising aldehydes with a catalyst inside a reactor to create a mixture and agitating the mixture at a temperature in a range of between about 200° F. to about 275° F. to create a reacted mixture. The method further comprises cooling the reacted mixture in the reactor to phase separate the reacted mixture into an organic phase and an aqueous phase, removing the organic phase out of the reactor, transferring the organic phase to a distillation tower, distilling the organic phase until mixed aldol products are isolated from hydroformylation products, and removing the mixed aldol products. The method may further comprise recycling the hydroformylation products by introducing them to the reactor.

These and other needs in the art are addressed by an additional embodiment that comprises a method for producing mixed aldol products from the products of hydroformylation reactions. The method comprises mixing hydroformylation products comprising aldehydes with a catalyst inside a reactor to create a mixture. The method also includes agitating the mixture at a temperature in a range of between about 200° F. to about 275° F. to create a reacted mixture. The method additionally includes cooling the reacted mixture in the reactor to create an organic phase and an aqueous phase. The method further includes distilling the organic phase in the reactor until mixed aldol products are isolated and removing the mixed aldol products.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
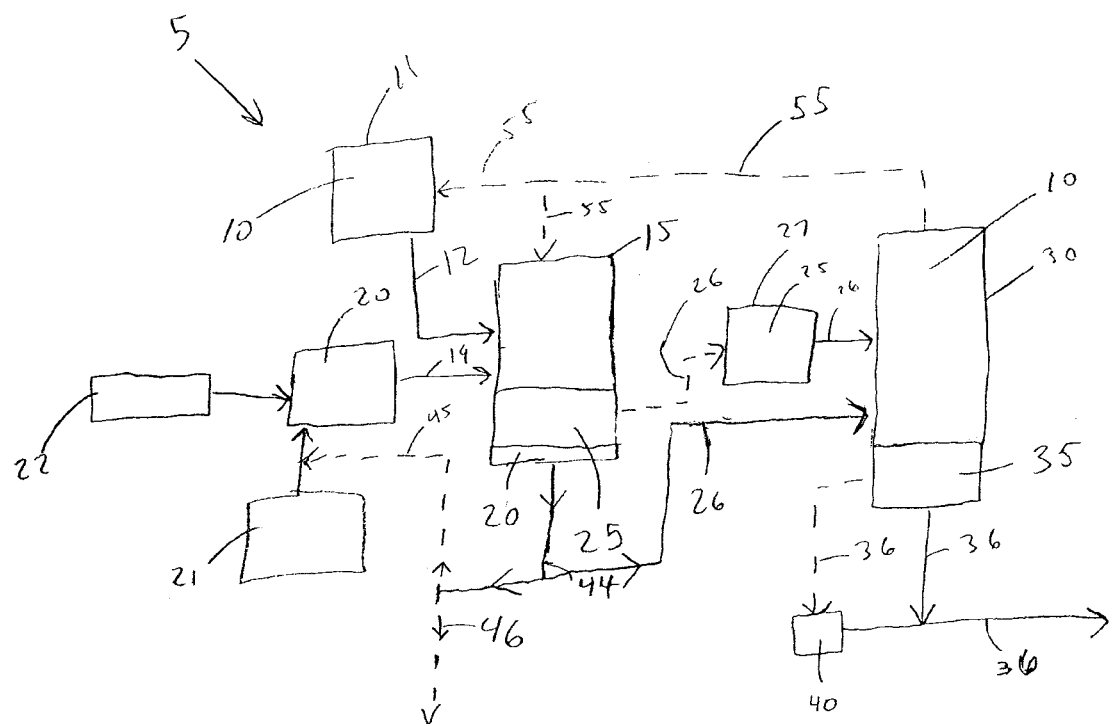
FIG. 1 illustrates a flow diagram of an embodiment of an aldol reaction process for the production of mixed aldol products from the products of hydroformylation reactions.

The present embodiments relate to the production of mixed aldol products, and more particularly, to methods and systems for producing mixed aldol products from the products of hydroformylation reactions. In embodiments, a mixture of products from a hydroformylation reaction is provided. The mixture may contain any products of a hydroformylation reaction and downstream reactions of products of these hydroformylation reactions. As used herein, the term "hydroformylation reaction products" refers to any such product produced from a hydroformylation reaction and downstream reactions of products of these hydroformylation reactions. A hydroformylation reaction is a reaction that produces aldehydes from alkenes. In embodiments, the hydroformylation reaction products may be, but are not limited to aldehydes, for example, acetaldehyde, propionaldehyde, isobutyraldehyde, butyraldehyde, 2-methyl-1-butanal, valeraldehyde, 2-methyl-2-pentanal; any products/byproducts of downstream reactions of products of these hydroformylation reactions; alcohols, for example, methanol, propanol, isobutyl alcohol, n-butyl alcohol, 2-methyl-1-butanol, or combinations thereof; carboxylic acids, for example acetic acid, propionic acid, butyric acid, pentanoic acid or combinations thereof esters, propylpropionate, butyl butyrate or combinations thereof; acetals, 1,1-dibutoxybutane, 1,1-dipropoxypropane or combinations thereof aldol products, for example 2-methyl-2-pentenal, 2-ethyl-2-hexenal, 2-propyl-2-heptenal and the like, or combinations thereof. In an embodiment, a hydroformylation reaction product is butyraldehyde. The hydroformylation reaction products may comprise hydroformylation reaction products that do not react in an aldol condensation reaction, for example, the hydroformylation reaction products may comprise an isomer which does not react to produce an aldol product, or alternatively, the hydroformylation products may react but do not produce an aldol product, defined herein as a $C_6$-$C_{20}$ $\alpha$, $\beta$-unsaturated aldehyde with a flashpoint greater than 110° F. These undesirable hydroformylation reaction products do not interfere with the aldol condensation reaction, and thus there is no need to selectively remove them. Further, the methods and systems disclosed herein may be performed efficiently and economically, without the need for specialized reagents (i.e., specialized catalysts) to produce selective products. The lack of reactant selectivity for the hydroformylation reaction products, increases the economic benefits as it eliminates the need for chemical separation and isolation steps, or the use of specific catalysts in the upstream hydroformylation reactions and downstream reactions of products of these hydroformylation reactions that may specifically select for, or increase the yield of only the reactive or desirable species or isomers of the hydroformylation reaction products. Therefore, a benefit of the disclosed methods is that they may not require modification of upstream or downstream processes in order to function efficiently. As such, any product stream, by-product stream, co-product stream, etc. from a hydroformylation reaction or downstream reactions such as hydrogenation, oxidation, esterification, aldol condensation on hydroformylation products may be used without regards to content and concentration of the individual hydroformylation reaction product species, provided said streams surpass a threshold amount of economic viability for at least one of the reactive hydroformylation product species contained within the streams.

Without limitation, a portion of the hydroformylation reaction products may be converted to mixed aldol products, (i.e., $C_6$-$C_{20}$ $\alpha$, $\beta$-unsaturated aldehydes) with flashpoints greater than 110° F. "Mixed aldol products" as used herein refers to products produced from aldol condensation reactions. In embodiments, the mixed aldol products may be, but are not limited to aldehydes such as 2-ethyl-2-hexenal, 2-propyl-2-hexenal, ethyl-heptanal, 2-propyl-2-heptenal, 2-ethyl-2-heptenal, 2-ethyl-2-pentenal, 2-methyl-2-pentenal, 2-isopropylbut-2-enal, methyl-heptanal, 2-methyl-2-heptenal, ethyl-octenal; ethers such as 1-methoxy-2-heptyne; the like, or combinations thereof. In an embodiment, a mixed aldol product may be 2-ethyl-2-heptenal. The mixed aldol products may be used as reactants, as fuel sources, or further refined for downstream applications.

The hydroformylation reaction products may react in an aldol condensation reaction to form the mixed aldol products. In embodiments, the hydroformylation reaction products may be any such combination of species of hydroformylation reaction products. In embodiments, a hydroformylation reaction product may react with the same species of hydroformylation product (i.e., a self-aldol condensation), alternatively, a hydroformylation reaction product may react with a different species of hydroformylation reaction product (i.e., a cross-aldol condensation), or a combination thereof. Equation 1 below, is an example embodiment of a (same species) self-aldol condensation reaction using butyraldehyde, a hydroformylation reaction product, as both of the reactants; whereas equation 2A and equation 2B below, are examples of a (mixed species) cross-aldol condensation reaction using butyraldehyde and propionaldehyde, both of which are hydroformylation reaction products, as the reactants. As illustrated below, the reactions may produce 2 different aldol products.

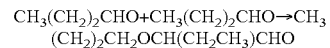

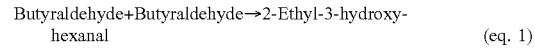 (eq. 1)

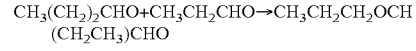

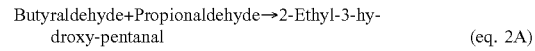 (eq. 2A)

or $$CH_3(CH_2)_2CHO+CH_3CH_2CHO \rightarrow CH_3(CH_2)_2CH_2OCH(CH_3)CHO$$

Butyraldehyde+Propionaldehyde→2-Methyl-3-hydroxy-hexanal (eq. 2B)

Both example reactions complete the aldol condensation reaction by undergoing a subsequent dehydration reaction as illustrated by equations 3, 4A, and 4B respectively:

$$CH_3(CH_2)_2CH_2OCH(CH_2CH_3)CHO \rightarrow CH_3(CH_2)_2CHC(CH_2CH_3)CHO+H_2O$$

2-Ethyl-3-hydroxy-hexanal→2-Ethyl-2-hexenal+Water (eq. 3)

$$CH_3CH_2CH_2OCH(CH_2CH_3)CHO \rightarrow CH_3CH_2CHC(CH_2CH_3)CHO+H_2O$$

2-Ethyl-3-hydroxy-pentanal→2-Ethyl-2-pentenal+Water (eq. 4A)

or $$CH_3(CH_2)_2CH_2OCH(CH_3)CHO \rightarrow CH_3(CH_2)_2CHC(CH_3)CHO+H_2O$$

2-Methyl-3-hydroxy-hexanal→2-Methyl-2-hexenal+Water (eq. 4B)

Eq. 1 and 3 can be combined as illustrated by Equation 5:

$$CH_3(CH_2)_2CHO+CH_3(CH_2)_2CHO \rightarrow CH_3(CH_2)_2CHC(CH_2CH_3)CHO+H_2O$$

Butyraldehyde+Butyraldehyde→2-Ethyl-2-hexenal+Water (eq. 5)

In embodiments, the above reactions may be catalyzed by a base, for example, sodium hydroxide. The dehydration reaction may be induced by heat. Dependent upon the reaction variables, any of the aldol products (e.g., those illustrated in the above examples, $C_8H_{14}O$ and $C_8H_{12}O$), may also comprise any such possible isomer and should not be limited to one structure.

FIG. 1 illustrates a flow diagram of an embodiment of an aldol reaction process 5 for the production of mixed aldol products 35 from the products of hydroformylation reactions. The aldol reaction process 5 comprises hydroformylation reaction products 10. Without limitation, hydroformylation reaction products 10 may comprise any such products of a hydroformylation reaction including aldehydes, for example, acetaldehyde, propionaldehyde, isobutyraldehyde, butyraldehyde, 2-methyl-1-butanal, valeraldehyde, 2-methyl-2-pentenal, or combinations thereof; products of downstream reactions of hydroformylation products including alcohols, for example, methanol, ethanol, propanol, isobutyl alcohol, n-butyl alcohol, 2-methyl-1-butanol, 1-pentanol and 3-pentanol or combinations thereof; carboxylic acids like propionic, butyric and pentanoic acids or combinations thereof; esters such as propylpropionate, butyl butyrate or combinations thereof and any other products of any hydroformylation reaction or a combination thereof. Hydroformylation reaction products 10 may be present in any concentration and in any ratio. For example hydroformylation reaction products 10 may comprise methanol in an amount between about 0.001% to about 10% by volume, or further in an amount between about 0.01% to about 0.1% by volume; ethanol in an amount between about 0.001% to about 10% by volume, or further in an amount between about 0.01% to about 0.1% by volume; propionaldehyde in an amount between about 0.1% to about 15% by volume, or further in an amount between about 1% to about 10% by volume; propanol in an amount between about 0.01% to about 10% by volume, or further in an amount between about 0.1% to about 2.5% by volume; isobutyraldehyde in an amount between about 1% to about 15% by volume, or further in an amount between about 1% to about 5% by volume; butyraldehyde in an amount between about 1% to about 60% by volume, or further in an amount between about 20% to about 40% by volume; isobutyl alcohol in an amount between about 0.1% to about 15% by volume, or further in an amount between about 1% to about 8% by volume; 2-methyl-1-butanal in an amount between about 0.1% to about 15% by volume, or further in an amount between about 1% to about 10% by volume; n-butyl alcohol in an amount between about 0.1% to about 10% by volume, or further in an amount between about 1% to about 10% by volume; valeraldehyde in an amount between about 1% to about 50% by volume, or further in an amount between about 10% to about 40% by volume; 2-methyl-1-butanol in an amount between about 0.01% to about 1.0% by volume, or further in an amount between about 0.01% to about 0.1% by volume; 2-methyl-2-pentenal in an amount between about 0.01% to about 10% by volume, or further in an amount between about 0.01% to about 1% by volume; propionic acid in an amount between about 0.01% to about 2.0% by volume, or further in an amount between about 0.001% to about 1% by volume; butyric acid in an amount between about 0.01% to about 2.0% by volume, or further in an amount between about 0.001% to about 1% by volume; pentanoic acid in an amount between about 0.01% to about 2.0% by volume, or further in an amount between about 0.001% to about 1% by volume; propyl propionate in an amount between about 0.01% to about 2.0% by volume, or further in an amount between about 0.001% to about 0.01% by volume; butyl butyrate in an amount between about 0.01% to about 2.0% by volume, or further in an amount between about 0.001% to about 0.01% by volume. In an embodiment, the hydroformylation reaction products 10 comprise about 0.05% methanol, about 3% propionaldehyde, about 6.0% n-propanol, about 6% isobutyraldehyde, about 32% butyraldehyde, about 5% isobutyl alcohol, about 5% 2-methyl-1-butanal, about 2.50% n-butyl alcohol, about 20% valeraldehyde, about 0.05% 2-methyl-1-butanol, about 0.5% 2-methyl-2-pentenal propionic acid, about 0.001% butyric acid, about 0.001% pentanoic acid, about 0.001% propyl propionate, and about 0.001% butyl butyrate. As discussed above, the aldol condensation reaction of the hydroformylation reaction products 10 may produce mixed aldol products 35 which may be predominantly $C_6$-$C_{20}$ α,β-unsaturated aldehydes with flashpoints greater than 110° F. The mixed aldol products 35 are described in more detail below.

Hydroformylation reaction products 10 may be stored until desired for use. For example, hydroformylation reaction products 10 may be stored in any such manner such as within a tank or other suitable vessel. With reference to FIG. 1, hydroformylation reaction products 10 are disposed within feed supply 11. Feed supply 11 is a vessel capable of containing hydroformylation reaction products 10. Hydroformylation reaction products 10 may be introduced to reactor 15 via supply stream 12. Supply stream 12 may be any such conduit capable of transporting hydroformylation reaction products 10. Supply stream 12 may be composed of metal, plastic, the like, and composites thereof. Hydroformylation reaction products 10 may be introduced to reactor 15 by any suitable means such as by a pump (not shown). Reactor 15 may be any reactor sufficient for containing any reaction comprising hydroformylation reaction products 10. Embodiments of reactor 15 may include, but should not be limited to, batch reactors, semi-batch reactors, tubular reactors, continuous reactors, and the like. In an embodiment, reactor 15 is a carbon steel batch reactor. In optional embodiments, reactor 15 can be stainless steel, glass lined steel, inconel, or combinations thereof; 15 may be jacketed, may comprise heating and/or cooling systems, may be provided with an overhead condenser, may comprise a circulating pump or other type of pump, may comprise mixing systems, agitation systems, heat exchanger systems, or any combination thereof. Reactor 15 may be made of any material sufficient for reacting hydroformylation reaction products 10, without limitation, these materials may include carbon steel, stainless steel (of any grade), the like and combinations or composites thereof.

Aldol reaction process 5 may comprise catalyst 20. Catalyst 20 may be pumped into reactor 15 to react with hydroformylation reaction products 10 via catalyst supply stream 19. Catalyst supply stream 19 may be any such conduit capable of transporting catalyst 20. Catalyst supply stream 19 may be composed of metal, plastic, the like, and composites thereof. Catalyst 20 may comprise any sufficient base for catalyzing any aldol condensation reaction of the hydroformylation reaction products 10. Embodiments of catalyst 20 may include, but should not be limited to, sodium hydroxide, potassium hydroxide, ammonium hydroxide, sodium carbonate, sodium bicarbonate, potassium carbonate, potassium bicarbonate, the like, or any combination thereof. In an embodiment catalyst 20 is sodium hydroxide. Catalyst 20 may be stored until desired for use. Catalyst 20 may be produced from a concentrated catalyst source 21, separate from and diluted with water 22 to achieve a desired range of strength, for example between about 0.1° A (w/w) to about 20% (w/w) of catalyst 20, alternatively about 1% (w/w) to about 10% (w/w) of catalyst 20, or further alternatively about 2% (w/w) to about 5% (w/w) of catalyst 20. The concentrated catalyst source 21 may comprise catalyst 20 in a higher concentration than the concentration used in reactor 15. For example concentrated catalyst source 21 may comprise catalyst 20 in a concentration between about 20% to about 80% by weight. In an embodiment, concentrated catalyst source 21 may comprise catalyst 20 in an amount of 50% by weight. The order of addition of hydroformylation reaction products 10 and catalyst 20 to reactor 15 may be in any desired order. As discussed above, hydroformylation reaction products 10 may be added to reactor 15 before catalyst 20. In alternative embodiments, catalyst 20 may be added to reactor 15 before hydroformylation reaction products 10. In further alternative embodiments. hydroformylation reaction products 10 and catalyst 20 may be added to reactor 15 simultaneously. The ratio of hydroformylation reaction products 10 to catalyst 20 is in a range of between about 10:1 to about 1:10, with higher concentrations of catalyst, alternatively about 5:1 to about 1:5, or further alternatively about 1:2 to about 2:1. For example, 50% (v/v) of 2% (w/w) concentration NaOH may yield higher amounts of aldol products than 10% (v/v) of 2% (w/w) concentration NaOH. Without being limited by theory, controlling the amount of catalyst 20 may limit the formation of undesirable products (i.e., aldehydes with carbon chains greater than 10). The amount of available catalyst 20 may be controlled by controlling the reaction time. The shorter the time less catalyst 20 is available and vice versa. As such, if there is insufficient catalyst 20 for the aldol condensation reaction, some of the hydroformylation reaction products 10 may not undergo the aldol condensation. If there is excess catalyst 20 the mixed aldol products formed in reactor 15 may undergo further reactions to produce undesirable C-10 to C-20 products. Therefore, using an optimal amount of catalyst 20 increases the selectivity of the mixed aldol products.

With continued reference to FIG. 1, once hydroformylation reaction products 10 and catalyst 20 have been introduced to reactor 15, hydroformylation reaction products 10 and catalyst 20 are agitated in reactor 15 for a time period sufficient to form crude reaction products 25. The time period may be any time period necessary to react a desired amount of hydroformylation reaction products 10. The time period may be between about 30 minutes to about 10 hours, alternatively about 1 hour to about 8 hours, and further alternatively about 2 hours to about 4 hours. In an embodiment, the time period is between about 2 hours to 4 hours. The reaction of the hydroformylation reaction products 10 may be at any pressure sufficient to react a desired amount of hydroformylation reaction products 10. The pressure in reactor 15 may be greater than ambient pressure, greater than 20 psig, greater than 30 psig, greater than 40 psig, greater than 50 psig, and so forth. In an embodiment, the pressure is greater than 40 psig. The reaction of the hydroformylation reaction products 10 may be at any temperature sufficient to react a desired amount of hydroformylation reaction products 10. The temperature in reactor 15 may be between about 150° F. to about 225° F., about 175° F. to about 250° F., about 200° F. to about 275° F., or alternatively, about 250° F. to about 325° F. and so on. In an embodiment, the temperature in the reactor 15 is between about 200° F. to about 275° F. In another embodiment, the reaction of the hydroformylation reaction products 10 is for a time period of between about 2 hours to about 4 hours at a temperature in a range of about 200° F. to about 275° F. (i.e. greater than 90° C.) and at a pressure in a range from ambient pressure to greater than 40 psig. It is to be understood, however, that the reaction time, temperature of the reaction, and the pressure inside the reactor 15 are dependent upon the size of reactor 15, the type of reactor 15, and the equipment available. The length of time for the reaction of the hydroformylation reaction products 10, the temperature inside the reactor 15, and the pressure inside the reactor 15, may all fall outside the ranges disclosed above should the size of reactor 15, the type of reactor 15, and the equipment available warrant adjustment of the above parameters in order to react a desired amount of the hydroformylation reaction products 10.

The agitation of the hydroformylation reaction products 10 and catalyst 20 in reactor 15 may be performed by any sufficient means and in any sufficient manner. Examples of agitation means may include, but are not limited to an agitator arrangement which is a centrally mounted driveshaft with impeller blades mounted on the shaft and provided with a fixed speed or variable speed drive unit on the top; paddles; baffles within the reactor itself, fins, stirring rods, circulation pumps, and the like. Examples of manners of agitation may include, but are not limited to sonication, vibration, stirring, pumping, and the like. The intensity of and the duration of the agitation used may be a function of the temperature in the reactor 15, duration of the reaction, the pressure inside the reactor 15, the volume of the reaction mixture in the reactor, the type of reactor 15, the equipment available fixed speed versus variable speed drive units, the type of and concentration of the hydroformylation products 10, and/or the amount of mixed aldol products desired. With the benefit of this disclosure, one of ordinary skill in the art will be able to select and implement an appropriate agitation means and manner.

Alternative embodiments may comprise an optional phase transfer catalyst instead of or in addition to heating the reaction of the hydroformylation reaction products 10. Examples of the phase transfer catalysts may include, but are not limited to tetra butyl ammonium bromide, tetra butyl ammonium hydrogen sulfate, benzyltrimethylammonium chloride, hexadecyltributylphosphonium bromide, methyltrioctylammonium chloride, crown ethers, polyethylene glycols, the like or combinations thereof. The phase transfer catalyst may be used to transfer the basic catalyst, say sodium hydroxide for instance, from the aqueous phase to the hydroformylation reaction products 10 in the organic phase; that is from one phase to another (i.e., from the aqueous phase to the non-aqueous phase). In some optional embodiments, the phase transfer catalyst may increase the reaction rate and/or increase the yield. The phase transfer catalyst may be included in any sufficient amount. For example, the phase transfer catalyst may be present in reactor 15 in an amount of about 0.1% to about 10% by volume, about 1% to about 8% by volume, or alternatively about 2% to about 5% by volume. In an embodiment the phase transfer catalyst is present in an amount of about 2% by volume.

After the reaction of the hydroformylation reaction products 10 has proceeded for the desired time and/or produced a sufficient yield, the reaction mixture may be cooled to allow the contents of the reactor to phase separate into an aqueous layer and an organic layer. The organic layer comprises crude reaction products 25, and the aqueous layer may comprise catalyst 20. The cooling may be accomplished inside reactor 15 or optionally, product discharge stream 26 may transfer the reaction products to a cooling vessel 27. The cooling may be performed by any sufficient means and in any sufficient manner. Examples of cooling may include, but are not limited to refrigeration, heat transfer, recirculation, dry cooling, the like, or combinations thereof. The amount of and the duration of the cooling used may be a function of the temperature in the reactor 15, time of the reaction, the pressure inside the reactor 15, the type of reactor 15, the equipment available. In embodiments, comprising a cooling reactor 15, the reactor 15 may be jacketed. The jacketed reactor 15 may comprise a fluid circulation means, such that heat may be transferred either to or from the circulating fluid. The cooling vessel 27 may be any such vessel suitable for cooling the finished reaction products. Cooling vessel 27 may include, but not be limited to a tank, jacketed tank, or tank with cooling coils and the like. With the benefit of this disclosure, one of ordinary skill in the art will be able to select and implement an appropriate cooling means and manner. In embodiments comprising a phase transfer catalyst and limited or no heating, the reaction products may not be cooled to separate into an aqueous and organic layer.

As discussed above, the crude reaction products 25 is obtained by cooling the aldol condensation reaction mixture, stopping the agitation and allowing the contents of the reactor to phase separate to an aqueous and organic layer, with the crude reaction products 25 residing in the organic layer. The aldol condensation reaction mixture may be cooled to any suitable temperature for any length of time necessary to allow phase separation of the reaction mixture into aqueous and organic layers. For example, cooling may comprise cooling to a temperature of about 100° F. to about 125° F., about 125° F. to about 150° F., or about 150° F. to about 175° F. for a sufficient time to induce separation into an aqueous phase and an organic phase. In an embodiment, the products of the aldol condensation reaction are cooled to about 150° F. to about 175° F.

The crude reaction products 25 comprise the mixed aldol products 35 and unreacted hydroformylation reaction products 10. As described above, the mixed aldol products 35 may comprise $C_6$-$C_{20}$ aldehydes with flashpoints greater than 110° F. Without limitation, specific examples of mixed aldol products 35 present in crude reaction products 25 may include 2-ethyl-2-heptenal (about 2% to about 25%), 2-ethyl-2-hexenal (about 5% to about 50%), 2-propyl-2-heptenal (about 5% to about 50%), 2-ethyl-2-pentenal (about 0.5% to about 5%), 2-methyl-2-heptenal (about 0.5% to about 5%), 2-propyl-2-hexenal (about 2 to about 25%), 1,2-methyl-2-hexenal, 2-methyl-2-pentenal (about 0.5% to about 3%), 2-propyl-2-pentenal (about 0.5% to about 5%), ethyl octenal (about 0.5% to about 5%), the like, or any combinations thereof. In addition, the crude reaction products 25 may also contain any unreacted hydroformylation reaction products 10 including but not limited to methanol (about 0.5%), propionaldehyde (about 0.5%), n-propanol (about 1% to about 7.5%), isobutyraldehyde (about 2.5%), butyraldehyde (about 0.5%), isobutyl alcohol (about 1% to about 7.5%), 2-methyl-1-butanal (about 1% to about 7.5%), n-butyl alcohol (about 1% to about 7.5%), valeraldehyde (about 1.5%), 2-methyl-1-butanol (about 0.5%), propionic acid, butyric acid, pentanoic acid, propyl propionate, and butyl butyrate. The crude reaction products 25 may be stored. The crude reaction products 25 may be stored in any suitable vessel including reactor 15 or cooling vessel 27. In optional embodiments, crude reaction product 25 may be tested, for example, by a gas chromatogram to confirm a sufficient amount of mixed aldol products 35 are present in the organic phase. In embodiments where the crude reaction products 25 are tested, for example by gas chromatography, a typical aldol condensation reaction may be deemed to be complete when the sum of the concentrations of certain unreacted hydroformylation reaction products 10 (e.g., propionaldehyde, butyraldehyde and valeraldehyde) are present in a desirable amount, for example, amount of less than about 10%, and alternatively less than 2% of the organic layer. The remaining amount of unreacted hydroformylation reaction products 10 is to be determined by one of ordinary skill in the art and may be dependent upon the economics of the process. If reactor 15 is of suitable size and capability, reactor 15 may be able to continuously react the hydroformylation reaction products 10 to continuously produce the crude reaction products 25.

Crude reaction products 25 may be transferred to a product separator 30 via reactor discharge stream 44 and then to product discharge stream 26. Product separator 30 may be any type of separating apparatus capable of separating any unreacted hydroformylation reaction products 10 from the mixed aldol products 35. Examples of product separator 30 may include, but are not limited to distillation towers, flash drums, batch reactors, thin film or wiped film evaporators, and the like. Separation methods include, but are not limited to, distillation, flashing the crude reaction product, and the like. In embodiments where product separator 30 comprises a distillation tower, distillation may be performed at temperatures in a range of between about 200° F. to about 400° F. or higher and at a vacuum of 24" to 28" of Hg with a 1:1 reflux. Optionally, nitrogen sparging and/or vacuuming may be used in the product separation process to aid in the stripping of any unreacted hydroformylation reaction products 10.

With further reference to FIG. 1, after the crude reaction products 25 are separated into the mixed aldol products 35 and any remaining hydroformylation reaction products 10 in the product separator 30, the mixed aldol products 35 may be removed from the product separator 30 via aldol product stream 36. Optionally, testing 40 (e.g., gas chromatography, Pensky-Martens closed-cup flash-point test) may be performed on the mixed aldol products 35, before or after removal from product separator 30 to confirm that the desired mixed aldol products 35 are present and that the mixed aldol products 35 comprise flash points greater than about 110° F., for example greater than about 120° F., greater than about 130° F., greater than about 140° F., greater than about 150° F., greater than about 160° F., and so on. Testing 40 may comprise any type of testing and for any desired purpose. For example, testing 40 may include, but should not be limited to gas chromatography, Pensky-Martens closed-cup flash-point test, mass spectrometry, nuclear magnetic resonance, infrared spectroscopy, UV spectroscopy, pH testing, Boiling point range, and the like or combinations thereof. Mixed aldol products 35 may comprise $C_6$-$C_{20}$ aldehydes with flashpoints greater than 110° F. Without limitation, specific examples of mixed aldol products 35 include 2-ethyl-2-heptenal (about 2% to about 25%), 2-ethyl-2-hexenal (about 5% to about 50%), 2-propyl-2-heptenal (about 5% to about 50%), 2-ethyl-2-pentenal (about 0.5% to about 5%), 2-methyl-2-heptenal (about 0.5% to about 5%), 2-propyl-2-hexenal (about 2 to about 25%), 1,2-methyl-2-hexenal, 2-methyl-2-pentenal (about 0.5% to about 3%), about 2-propyl-2-pentenal (about 0.5% to about 5%), ethyl octenal (about 0.5% to about 5%), the like, derivatives (e.g., dimers), or any combinations thereof. In some embodiments, testing 40 may not be done.

Aldol product stream 36 comprises the mixed aldol products 35 removed from product separator 30. Aldol product stream 36 may be stored, for example, in a tank or a vessel. Alternatively aldol product stream 36 may be conveyed via conduit, or any other suitable transport conveyance, for use in any suitable downstream application. Downstream applications may include, heating oils, fuel oil, combustibles, use in further processing and refinement, stock for manufacturing feeds, etc. With the benefit of this disclosure, one of ordinary skill in the art will be able to use the mixed aldol products 35 disclosed herein in a desired application.

With continued reference to FIG. 1, mixed aldol reaction process 5 provides for the optional recycling of any unreacted hydroformylation reaction products 10 as well as the recycling of catalyst 20. In optional embodiments, hydroformylation recycle stream 55, conveys any remaining hydroformylation reaction products 10 from the product separator 30 to either the feed supply 11 of the hydroformylation reaction products 10 or to the reactor 15 as desired. In embodiments where hydroformylation recycle stream 55 transports any unreacted hydroformylation reaction products 10 to the feed supply 11, the unreacted hydroformylation reaction products 10 may be mixed with any hydroformylation reaction products 10 in feed supply 11 before being pumped to reactor 15 via feed supply stream 12. This process may be continuous or noncontinuous as desired. In embodiments where hydroformylation recycle stream 55 transports any unreacted hydroformylation reaction products 10 to the reactor 15, the unreacted hydroformylation reaction products 10 may be introduced to reactor 15 to react in an aldol condensation reaction. This process may be continuous or noncontinuous as desired. Optionally, testing (not shown) may be performed on any unreacted hydroformylation reaction products 10 at any point in the recycling process or in the product separator 30 if desired. The testing may be used to determine the content and concentrations of the various individual species of any unreacted hydroformylation reaction products 10. For example, testing 40 may comprise gas chromatography testing, to surmise the sum of the concentrations of specific unreacted hydroformylation reaction products 10 such as propionaldehyde, butyraldehyde and valeraldehyde. The unreacted hydroformylation reaction products 10 may be recycled via hydroformylation recycle stream 55. As discussed above, the testing 40 may comprise any type of testing and be used for any desired purpose. For example, the testing may include, but should not be limited to gas chromatography, mass spectrometry, nuclear magnetic resonance, the like, or combinations thereof.

As discussed above, the aqueous layer that phase separates in reactor 15 may comprise catalyst 20. In optional embodiments, catalyst 20 may be removed from reactor 15 via reactor discharge stream 44. In some embodiments, a portion, or the whole of the catalyst 20 removed via the reactor discharge stream 44 may be recycled through a catalyst recycle stream 45. In some embodiments, a portion, or the whole of the catalyst 20 removed via the reactor discharge stream 44 may be disposed of through a catalyst disposal stream 46. In some embodiments, a portion of catalyst 20 from reactor discharge stream 44 may be recycled through catalyst recycle stream 45 and a portion of catalyst 20 from reactor discharge stream 44 may be disposed of through catalyst disposal stream 46. In some embodiments, any portion of catalyst 20 that is recycled through catalyst recycle stream 45 may be mixed with a concentrated catalyst 20 from concentrated catalyst source 21. The recycled catalyst from the catalyst recycle stream 45 and the concentrated catalyst 20 from the concentrated catalyst source 21 may be diluted with water from water source 22 prior to introduction to the reactor 15. Catalyst disposal stream 46 may dispose of catalyst 20 in any suitable manner.

In embodiments where reactor 15 comprises a batch reactor, the reactor 15 may use agitation and/or heat to increase the yield of the aldol condensation reaction as described above. The reaction is a biphasic reaction. In some optional embodiments, the operation of the batch reactor does not include any other labor to be input to the process (e.g., monitoring flow rates of reactants, mixing of phases). As discussed above, any remaining hydroformylation reaction products 10 may be recycled after their separation from the mixed aldol products 35. Therefore, compared to other reactor types, a batch reactor may require the least operation input and oversight and may be the most economical choice. Further, in some embodiments, the mixed aldol reaction process 5 illustrated in FIG. 1 may not comprise any specific selectivity as to the mixed aldol products 35. Similarly, there may be no single preferred or desirable type and/or range of hydroformylation reaction products 10 to use as reactants, nor is any specific purity of hydroformylation reaction products 10 required; as such, the process is economical and efficient. Any product stream comprising any type, mixture, or ratio of hydroformylation reaction products 10 may be used, examples may include, but should not be limited to side-streams, by-product streams, and/or co-product streams. Thus, the aldol reaction process 5 disclosed herein may be utilized as a part of any other upstream or downstream process that produces hydroformylation reaction products 10, with no regards to the intent behind the production of the hydroformylation reaction products 10 or to the species or concentration of the hydroformylation reaction products 10. Therefore, there may be no need for modification of the aforementioned upstream or downstream process.

Figure 2:
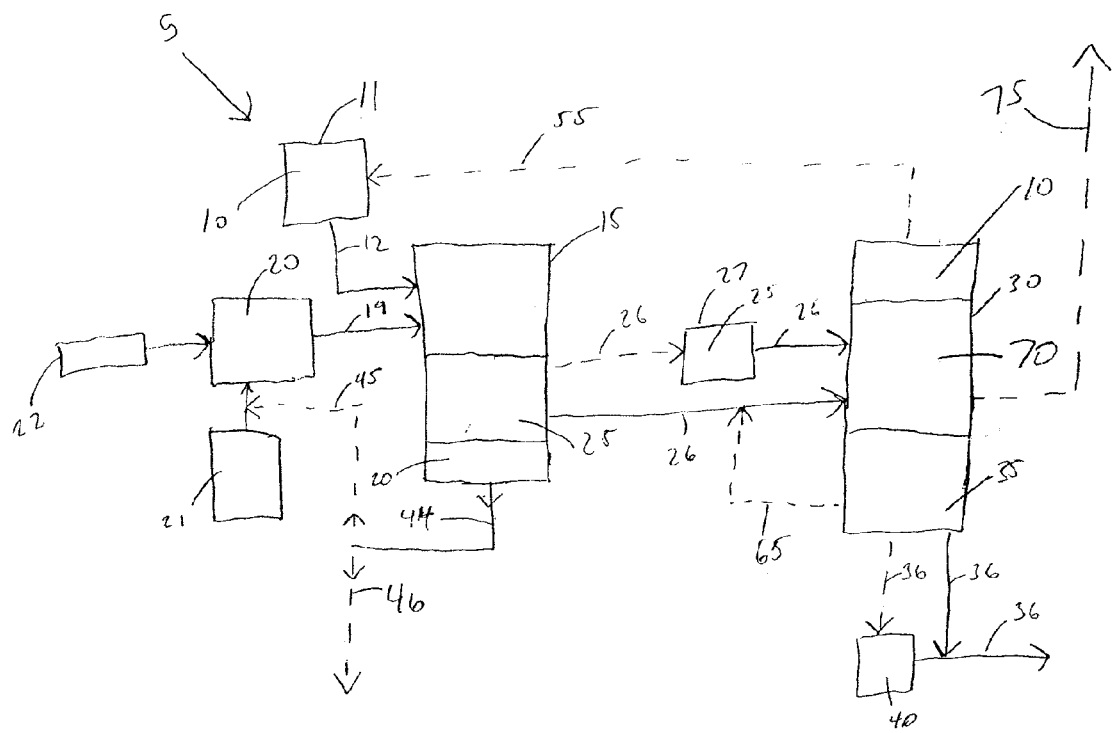
FIG. 2 illustrates a flow diagram of an embodiment of an aldol reaction process for the production of mixed aldol products from the products of hydroformylation reactions comprising additional recycling of any lighter unreacted reactants and the isolation of any mixed aldol products.

FIG. 2 illustrates a flow diagram of an embodiment of a aldol reaction process 5 as in FIG. 1, but with additional optional recycling of the crude reaction products 25 and the removal of mixed alcohol products 70 from product separator 30. In FIG. 2, hydroformylation reaction products 10 and catalyst 20 are added to reactor 15. Embodiments of the reaction and conditions of FIG. 2 are disclosed for the embodiments disclosed for FIG. 1, except for the noted recycling of crude reaction products 25 and the isolation and removal of the mixed alcohol products 70.

With continued reference to FIG. 2, product separator 30 allows for the separation and removal of mixed aldol products 35 and the recycling of any unreacted hydroformylation reaction products 10 via hydroformylation recycle stream 55. FIG. 2 also comprises the optional recycling of crude reaction products 25 from the product separator 30 via crude product recycle stream 65. Should a sufficient amount of crude reaction products 25 remain in product separator 30 after distillation is complete, the remaining crude reaction products 25 may be recycled via crude product recycle stream 65 to be mixed with crude reaction products 25 via the product discharge stream 26 where they may be distilled again via product separator 30. This process may be continuous or noncontinuous. The crude reaction products 25 may continue to be recycled as desired.

Continuing with FIG. 2, mixed alcohol products 70 may be removed from product separator 30 via mixed alcohol removal stream 75. Mixed alcohol products 70 may comprise a mixture of $C_1$-$C_5$ alcohols. Without being limited by theory, mixed alcohol products 70 may be free of or mostly free of aldehydes. In some optional embodiments it may contain any or all of methanol (about 0.5%), n-propanol (about 1% to about 7.5%), isobutyl alcohol (about 1 to about 7.5%), n-butyl alcohol (about 1 to about 7.5%), 2-methyl-1-butanol (about 0.5%). Mixed alcohol products 70 may be stored until desired for use, for example in a downstream application. Mixed alcohol products 70 may be stored in any such manner such as within a tank or other suitable vessel. Mixed alcohol products 70 may also be transported for use in any downstream application. Downstream applications may include, fuel sources, incineration agents, use in further processing and refinement, stock for manufacturing feeds, etc. The isolation and subsequent removal of the mixed alcohol products 70 may be a continuous or noncontinuous process. The mixed alcohol products 70 may continue to be recycled as desired. With the benefit of this disclosure, one of ordinary skill in the art will be able to isolate, remove, and use the mixed alcohol products 70 disclosed herein in a desired application.

Figure 3:
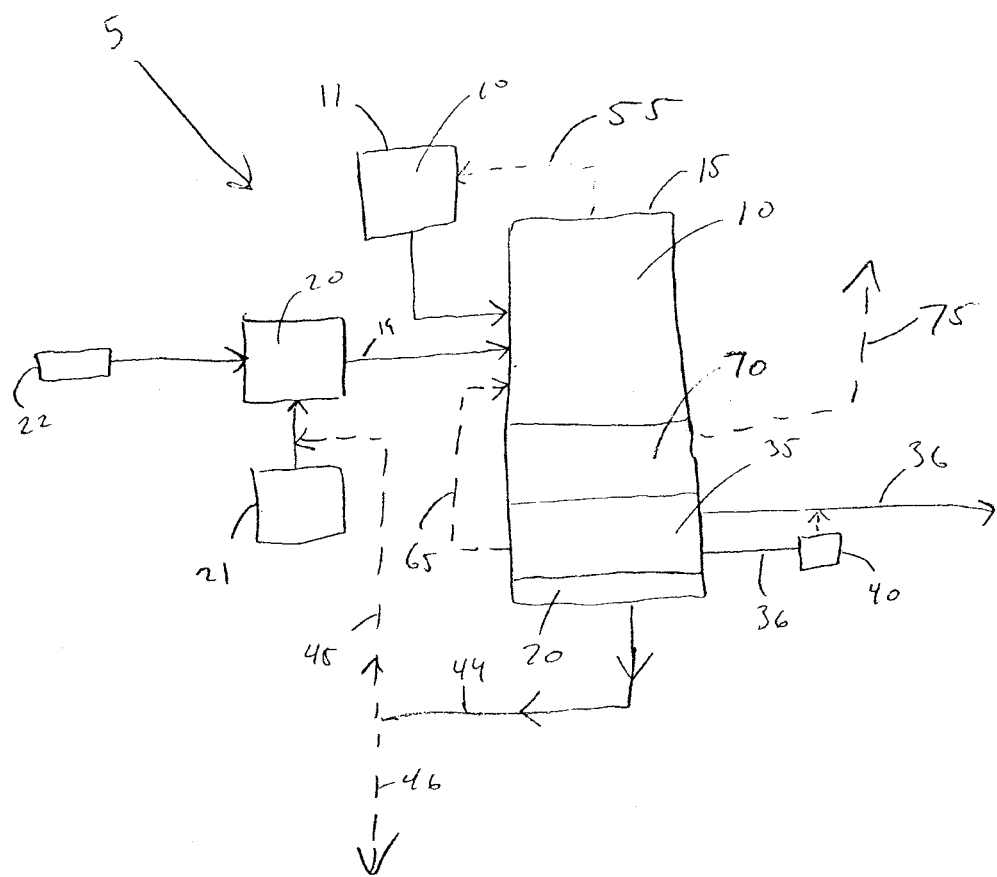
FIG. 3 illustrates a flow diagram of an embodiment of an aldol reaction process for the production of mixed aldol products from the products of hydroformylation reactions comprising a reactor that is capable of product separation.

FIG. 3 illustrates a flow diagram of an embodiment of an aldol reaction process 5 as in FIG. 1, but in FIG. 3, reactor 15 additionally functions as a product separator, analogous to product separator 30 as illustrated in FIGS. 1 and 2. As in FIG. 1, hydroformylation reaction products 10 and catalyst 20 are added to reactor 15. Embodiments of the reaction and reaction conditions of FIG. 3 are disclosed in the embodiments disclosed in FIGS. 1 and 2. As illustrated in FIG. 3, reactor 15 reacts the hydroformylation reaction products 10 in an aldol condensation reaction as shown in FIGS. 1 and 2, and also separates the crude reaction products 25 into mixed aldol products 35, remaining hydroformylation reaction products 10 (if present), and mixed alcohol products 70. As such, the crude reaction products 25 are not transferred to a separate product separator 30. As described in FIGS. 1 and 2, the catalyst 20 and the unreacted hydroformylation reaction products 10 may be recycled if desired via catalyst recycle stream 45 and hydroformylation recycle stream 55 respectively. Analogously to FIG. 2, the crude reaction products 25 may be recycled via crude product recycle stream 65 and reintroduced to reactor 15. Further, as described in FIG. 2, the reactor 15 may separate any mixed alcohol products 70 from the crude reaction products 25 and the mixed alcohol products 70 may be removed from reactor 15 via alcohol removal stream 75.

In the embodiment of FIG. 3, reactor 15 may function as any type of product separator described herein, including a distillation tower. In some embodiments, reactor 15 may react the hydroformylation reaction products 10 in an aldol condensation reaction and then separate the crude reaction products 25 into the mixed aldol products 35, remaining hydroformylation reaction products 10 (if present), and mixed alcohol products 70 in a continuous process. In alternative embodiments, reactor 15 may react the hydroformylation reaction products 10 in an aldol condensation reaction and then separate the crude reaction products 25 into the mixed aldol products 35, remaining hydroformylation reaction products 10 (if present), and mixed alcohol products 70 in a noncontinuous process.

To facilitate a better understanding of the present disclosure, the following examples of some specific embodiments are given. In no way should the following examples be read to limit, or to define, the scope of the invention.

EXAMPLE 1

Example 1 illustrates eight example reactions with varying reaction conditions. Each reaction was performed in a Parr® stirred reactor. Parr® is a registered trademark of Parr Instrument Company. The reactants were various species of hydroformylation reaction products, obtained from hydroformylation reactions and downstream reactions of hydroformylation products. The catalyst was NaOH. The hydroformylation reaction products and the catalyst were individually added to the stirred reactor. Eight experimental reactions were conducted with varying experimental conditions. For example, the temperature was varied, as was the amount of hydroformylation products, and the amount and concentration of the catalyst. The experimental parameters for each reaction are presented in Table 1 below.

TABLE 1

|  | Rxn. 1 | Rxn. 2 | Rxn. 3 | Rxn. 4 | Rxn. 5 | Rxn. 6 | Rxn. 7 | Rxn. 8 |
| --- | --- | --- | --- | --- | --- | --- | --- | --- |
| Total Hydroformylation Products (mL) | 1000 | 1350 | 1300 | 1300 | 1300 | 1200 | 1200 | 1100 |
| Catalyst Amount in Reaction (mL) | 500 | 135 | 195 | 195 | 195 | 240 | 300 | 330 |
| Catalyst Concentration wt. % | 2% | 2% | 2% | 2% | 5% | 2% | 2% | 2% |

TABLE 1-continued

|  | Rxn. 1 | Rxn. 2 | Rxn. 3 | Rxn. 4 | Rxn. 5 | Rxn. 6 | Rxn. 7 | Rxn. 8 |
| --- | --- | --- | --- | --- | --- | --- | --- | --- |
| Temperature (° C.) | 125 | 125 | 120 | 100 | 120 | 120 | 120 | 120 |
| pH of aqueous layer after reaction | 14 | 8 | 10 | 10 | 13 | 11 | 11 | 12 |

The aqueous layer comprises the NaOH and the amount of NaOH determines the pH of the aqueous layer. The percentages of the individual components of the hydroformylation reaction products were determined before addition to the stirred reactor. Additionally, the amounts of the components of the crude reaction product were determined after the reactions were completed and compared to the measurements of the hydroformylation reaction products. Moreover, the amount of mixed aldol products produced was also computed for each reaction to gauge the effect of the experimental parameters on the amount of mixed aldol product produced. The results are presented in Table 2 below.

TABLE 2

Individual Hydroformylation Products (wt. %)

|  | Initial | Rxn. 1 | Rxn. 2 | Rxn. 3 | Rxn. 4 | Rxn. 5 | Rxn. 6 | Rxn. 7 | Rxn. 8 |
| --- | --- | --- | --- | --- | --- | --- | --- | --- | --- |
| Acetaldehyde | 0.15 | 0.02 | 0.15 | 0.13 | 0.11 | 0.12 | 0.12 | 0.1 | 0.12 |
| Methanol | 0.09 | 0.01 | 0.02 | 0.03 | 0 | 0.01 | 0.03 | 0.01 | 0.02 |
| Propionaldehyde | 8.15 | 0.02 | 0.01 | 0.01 | 0.01 | 0.01 | 0.01 | 0.01 | 0.02 |
| Propanol/Isobutyraldehyde | 9.74 | 6.11 | 11.86 | 10.9 | 11.34 | 11.12 | 10.7 | 10.44 | 9.86 |
| Butyraldehyde | 33.94 | 0.5 | 3.09 | 0.66 | 0.83 | 0.71 | 0.42 | 0.45 | 0.22 |
| Isobutyl Alcohol | 4.16 | 4.67 | 5.39 | 5.26 | 5.42 | 5.45 | 5.28 | 5.62 | 5.73 |
| 2-methyl-butraldehyde/n-butanol | 6.96 | 5.16 | 10.31 | 7.08 | 7.26 | 7.22 | 7.05 | 6.98 | 6.91 |
| Valeraldehyde | 20.79 | 0.22 | 5.3 | 2.39 | 2.99 | 2.66 | 2.04 | 1.56 | 1.05 |
| 2-methyl-2-pentanal | 0.86 | 0.39 | 1.78 | 1.58 | 1.69 | 1.8 | 1.54 | 1.65 | 1.45 |
| Mixed Aldol Products | 8.16 | 78.9 | 58.09 | 67.96 | 66.35 | 66.9 | 67.81 | 69.18 | 69.82 |
| Water | 7 | 4 | 4 | 4 | 4 | 4 | 5 | 4 | 3.8 |
| Total | 100 | 100 | 100 | 100 | 100 | 100 | 100 | 100 | 99 |

Table 2 illustrates which of the individual hydroformylation reaction products may react to produce the mixed aldol products. Additionally, Table 2 illustrates that the reaction conditions of reaction 1 produced the largest amount of mixed aldol product.

The preceding description provides various embodiments of the systems and methods disclosed herein, which may contain different methods, steps and alternative combinations of components. It should be understood that, although individual embodiments may be discussed herein, the present disclosure covers all combinations of the disclosed embodiments, including, without limitation, the different component combinations, method step combinations, and properties of the system.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

Therefore, the present embodiments are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method for producing mixed aldol products from products of hydroformylation reactions, the method comprises:
   (A) mixing hydroformylation products comprising aldehydes with a catalyst inside a reactor to create a mixture;
   (B) agitating the mixture at a temperature in a range of between about 200° F. to about 275° F. to create a reacted mixture;
   (C) cooling the reaction mixture in the reactor to phase separate the reacted mixture into an organic phase and an aqueous phase;
   (D) removing the organic phase out of the reactor;
   (E) transferring the organic phase to a distillation tower;
   (F) distilling the organic phase until mixed aldol products are isolated, wherein the distilling is performed with a vacuum of 24 inches to 28 inches of mercury; and
   (G) removing the mixed aldol products.

2. The method of claim 1, wherein the hydroformylation products comprise methanol, propanol, isobutyl alcohol, n-butyl alcohol, 2-methyl-1-butanol, acetaldehyde, propionaldehyde, isobutyraldehyde, butyraldehyde, 2-methyl-1-butanal, valeraldehyde, 2-methyl-2-pentanal, or any combinations thereof.

3. The method of claim 1, wherein the catalyst is sodium hydroxide.

4. The method of claim 1, wherein a ratio of the hydroformylation products to the catalyst is in a range of between about 10:1 to about 1:10.

5. The method of claim 1, wherein the reactor is a batch reactor.

6. The method of claim 1, wherein the reaction temperature is between about 200° F. to about 240° F.

7. The method of claim 1, wherein the mixed aldol products comprise $C_6$ - $C_{20}$ aldehydes.

8. The method of claim 1, wherein the mixed aldol products comprise 2-ethyl-2-heptenal, 2-ethyl-2-hexenal, 2-propyl-2-heptenal, 2-ethyl-2-pentenal, 2-methyl-2-heptenal, 2-propyl-2-hexenal, 1, 2-methyl-2-hexenal, 2-methyl-2-pentenal, 2-propyl-2-pentenal, ethyl octenal, derivatives thereof, or any combinations thereof.

9. The method of claim 1, wherein the mixed aldol products have a flashpoint greater than 110° F.

10. The method of claim 1, further comprising a phase transfer catalyst.

11. The method of claim 10, wherein the phase transfer catalyst is tetra butyl ammonium bromide, tetra butyl ammonium hydrogen sulfate, or combinations thereof.

12. A method for producing mixed aldol products from products of hydroformylation reactions, the method comprises:
 (A) mixing hydroformylation products comprising aldehydes with a catalyst inside a reactor to create a mixture;
 (B) agitating the mixture at a temperature in a range of between about 200° F. to about 275° F. to create a reacted mixture;
 (C) cooling the reacted mixture in the reactor to phase separate the reacted mixture into an organic phase and an aqueous phase;
 (D) removing the organic phase out of the reactor;
 (E) transferring the organic phase to a distillation tower;
 (F) distilling the organic phase until mixed aldol products are isolated from hydroformylation products, wherein the distilling is performed with a vacuum of 24 inches to 28 inches of mercury;
 (G) removing the mixed aldol products; and
 (H) recycling the hydroformylation products by introducing them to the reactor.

13. The method of claim 12, further comprising removing spent catalyst from the reactor after step (C) and recycling the spent catalyst by mixing of the spent catalyst with an amount of a concentrated catalyst and then introducing the mixture to the reactor.

14. The method of claim 12, wherein the hydroformylation products comprise methanol, propanol, isobutyl alcohol, n-butyl alcohol, 2-methyl-1-butanol, acetaldehyde, propionaldehyde, isobutyraldehyde, butyraldehyde, 2-methyl-1-butanal, valeraldehyde, 2-methyl-2-pentanal, or any combinations thereof.

15. The method of claim 12, wherein the catalyst is sodium hydroxide.

16. The method of claim 12, wherein a ratio of the hydroformylation products to the catalyst is in a range of between about 10:1 to about 1:10.

17. The method of claim 12, wherein the reactor is a batch reactor.

18. The method of claim 12, wherein the reaction temperature is between about 200° F. to about 240° F.

19. The method in claim 12, wherein the mixed aldol products comprise $C_6$ - $C_{20}$ unsaturated aldehydes.

20. A method for producing mixed aldol products from products of hydroformylation reactions, the method comprises:
 (A) mixing hydroformylation products comprising aldehydes with a catalyst inside a reactor to create a mixture;
 (B) agitating the mixture at a temperature in a range of between about 200° F. to about 275° F. to create a reacted mixture;
 (C) cooling the reacted mixture in the reactor to phase separate the reacted mixture into an organic phase and an aqueous phase;
 (D) distilling the organic phase in the reactor until mixed aldol products are isolated, wherein the distilling is performed with a vacuum of 24 inches to 28 inches of mercury; and
 (E) removing the mixed aldol products.

* * * * *